United States Patent [19]

Marquez et al.

[11] Patent Number: 5,498,719

[45] Date of Patent: Mar. 12, 1996

[54] DIASTEREOSELECTIVE PROCESS LEADING TO A KEY INTERMEDIATE FOR THE PREPARATION OF FLUORINATED REVERSE TRANSCRIPTASE INHIBITORS

[75] Inventors: Victor E. Marquez, Gaithersburg; John S. Driscoll; Magbool A. Siddiqui, both of Rockville, all of Md.

[73] Assignee: The United States of America as represented by the Secretary of the Department of Health & Human Services, Washington, D.C.

[21] Appl. No.: 189,095

[22] Filed: Jan. 31, 1994

[51] Int. Cl.$^6$ ................................................. C07D 413/06
[52] U.S. Cl. ........................ 548/230; 548/186; 549/454; 549/475
[58] Field of Search .................................. 548/229, 230, 548/231, 232

[56] References Cited

U.S. PATENT DOCUMENTS

| | | | |
|---|---|---|---|
| 4,959,472 | 9/1990 | Wood et al. | 544/258 |
| 5,068,345 | 11/1991 | Illig et al. | 548/230 |
| 5,231,179 | 7/1993 | Terashima et al. | 548/230 |
| 5,264,577 | 11/1993 | Beylin et al. | 548/230 |
| 5,344,936 | 9/1994 | Silks et al. | 548/230 |

OTHER PUBLICATIONS

Evans et al., Tetrahedron vol. 44 pp. 5525–5540 (1988).
Okabe et al., J. Org. Chem., vol. 56, pp. 4392–4397 (1991).
Siddiqui et al. Tetra Lett. vol. 35, pp. 3263–3266 (1994).
Chamberlin, Chem. Abstr., vol. 111 Entry 1534690 (1989).

*Primary Examiner*—Donald G. Daus
*Attorney, Agent, or Firm*—Morgan & Finnegan

[57] ABSTRACT

The present invention provides a novel synthetic route to a key precursor, i.e., an (S,S)-α-fluoro-2,2-dimethyl-1,3-dioxolane-4-propanoic acid ester useful in the preparation of FddA and FddC. The instant diastereoselective process utilizes a novel intermediate which contains a chiral auxiliary. The chiral auxiliary can be any chiral auxiliary moiety such as for example an auxiliary containing a substituted oxazolidinone group. The intermediate containing the chiral auxiliary is fluorinated utilizing a fluorination method applied for the first time in the synthesis of fluorinated sugars to give a fluorinated intermediate which after removal of the chiral group provides the desired key intermediate. In summary, in the instant process, a fluorine is introduced diastereoselectively into an intermediate via the reaction of a chiral enolate with an electrophilic fluorinating agent and the intermediate which is fluorinated is derived from mannitol.

4 Claims, No Drawings

DIASTEREOSELECTIVE PROCESS LEADING TO A KEY INTERMEDIATE FOR THE PREPARATION OF FLUORINATED REVERSE TRANSCRIPTASE INHIBITORS

FIELD OF THE INVENTION

The present invention relates to a novel reaction sequence which is diastereoselective and economical and provides a key intermediate for the preparation of fluorinated reverse transcriptase inhibitors as well as novel compounds used to obtain the key intermediate.

BACKGROUND OF THE INVENTION

Various reverse transcriptase inhibitors have been found to be effective in inhibiting HIV reverse transcriptase. Amongst the more effective such inhibitors are 3'-deoxy-3'-azidothymidine (AZT), 2',3'-dideoxycytidine (ddC) and 2',3'-dideoxy-inosine (ddI).

A number of fluorinated 2',3'-dideoxynucleosides have been prepared in order to seek out biologically active and chemically stable agents that effectively inhibit HIV reverse transcriptase. Two very important fluorodideoxy nucleotides that function as HIV reverse transcriptase inhibitors are 9-(2,3-dideoxy-2-fluoro-β-D-threo-pentofuranosyl)-adenine (FddA) and 1-(2,3-dideoxy-2-fluoro-β-D-threo-pentofuranosyl) cytosine (FddC).

Since FddA is a promising candidate for the treatment of AIDS, various synthetic pathways have been tried to synthesize FddA. These processes are, however, expensive and there continues to be a need for a more economical procedure.

Okabe et al (J. Org. Chem. 1991,56,4392) have produced (S,S)-α-fluoro-2,2-dimethyl-1,3-dioxolane-4-propanoic acid methyl ester having the formula (I):

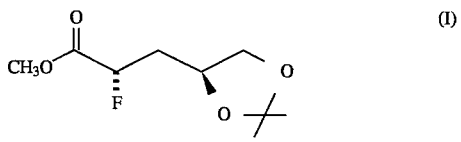

as a key intermediate for the synthesis of FddC. The Okabe et al synthesis of (I) begins with the inexpensive sugar D-xylose. However, the introduction of fluorine in the Okabe et al. synthesis was performed by leaving group displacement with fluoride ion which caused a loss of stereochemical control. This led to the formation of a mixture of diastereoisomers that required enrichment of the desired diastereoisomer by chemical or enzymatic means.

Since intermediate of formula (I) can be used to prepare both FddC and FddA, there remains a continuing need for a more efficient synthetic route to this intermediate in which there is essentially complete stereochemical control.

BRIEF DESCRIPTION OF THE INVENTION

The present invention relates to a novel synthetic route to a key precursor, i.e., an (S,S)-α-fluoro-2,2-dimethyl-1,3-dioxolane-4-propanoic acid ester having the formula (Ia).

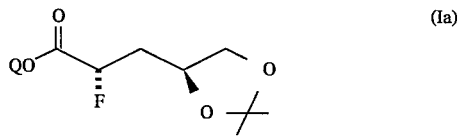

in which Q is a lower alkyl, $C_6$–$C_{12}$- aryl or $C_7$–$C_{13}$ aralkyl or alkaryl group.

The instant diastereoselective process utilizes a novel intermediate of formula (II)

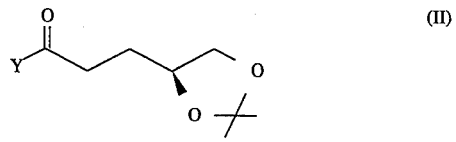

in which Y is a chiral auxiliary. The chiral auxiliary can be any chiral auxiliary moiety such as for example the oxazolidinone group of the formula,

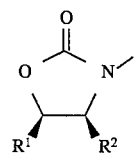

in which $R_1$ and $R_2$ each independently denote $C_6$ to $C_{12}$ aryl, $C_7$ to $C_{13}$ aralkyl or alkaryl or $C_1$ to $C_8$ alkyl or $R_1$ is H. $R_2$ cannot be H. The present invention encompasses compounds in which $R_1$ is H, methyl, ethyl, propyl, isopropyl, butyl, sec. butyl, tert. butyl, phenyl or benzyl and $R_2$ is methyl, ethyl, propyl, isopropyl, butyl, sec. butyl, tert. butyl, phenyl or benzyl. Another embodiment encompasses compounds in which $R_1$ is methyl and $R_2$ is phenyl or $R_1$ is phenyl and $R_2$ is methyl. Intermediate (II) is fluorinated utilizing a fluorination method applied for the first time in the synthesis of fluorinated sugars to give an intermediate of formula (III)

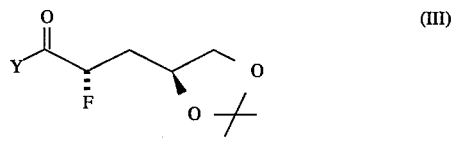

in which Y is as defined hereinabove and the chiral auxiliary is, for example, the oxazalidinone chiral auxiliary described, hereinabove.

In the instant process, a fluorine is introduced diastereoselectively into an intermediate of formula (II) via the reaction of a chiral enolate with an electrophilic fluorinating agent and the intermediate (II) is derived from mannitol.

DETAILED DESCRIPTION OF THE INVENTION

The instant process relates more specifically to an economic and diastereoselective synthetic route for the preparation of a key intermediate used to provide FddA or FddC of the formulae:

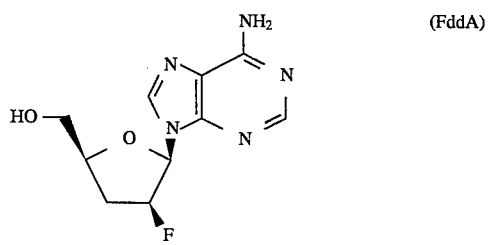

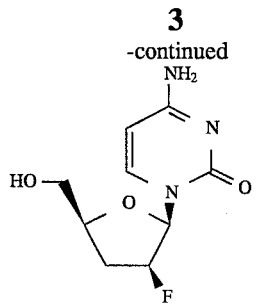

(FddC)

The intermediate of formula (Ia) is prepared in a preferred embodiment using an oxazolidinone chiral auxiliary as shown in accordance the following reaction scheme A.

tions. The stabilized ylide specifically exemplified herein is a known compound which is available from MTM Research Chemicals of Windham, N.H. The presence of the minor amount of trans-isomer is not relevant since the double bond is reduced in step c to give methyl (S)-4,5-O-isopropylidenepentanoate (VIIa). Reduction can be carried out by hydrogenation under pressure in the presence of known hydrogenation catalysts or any other known reduction procedure.

The combined yield over steps a, b and c of the instant reaction scheme is about 69%.

Scheme A

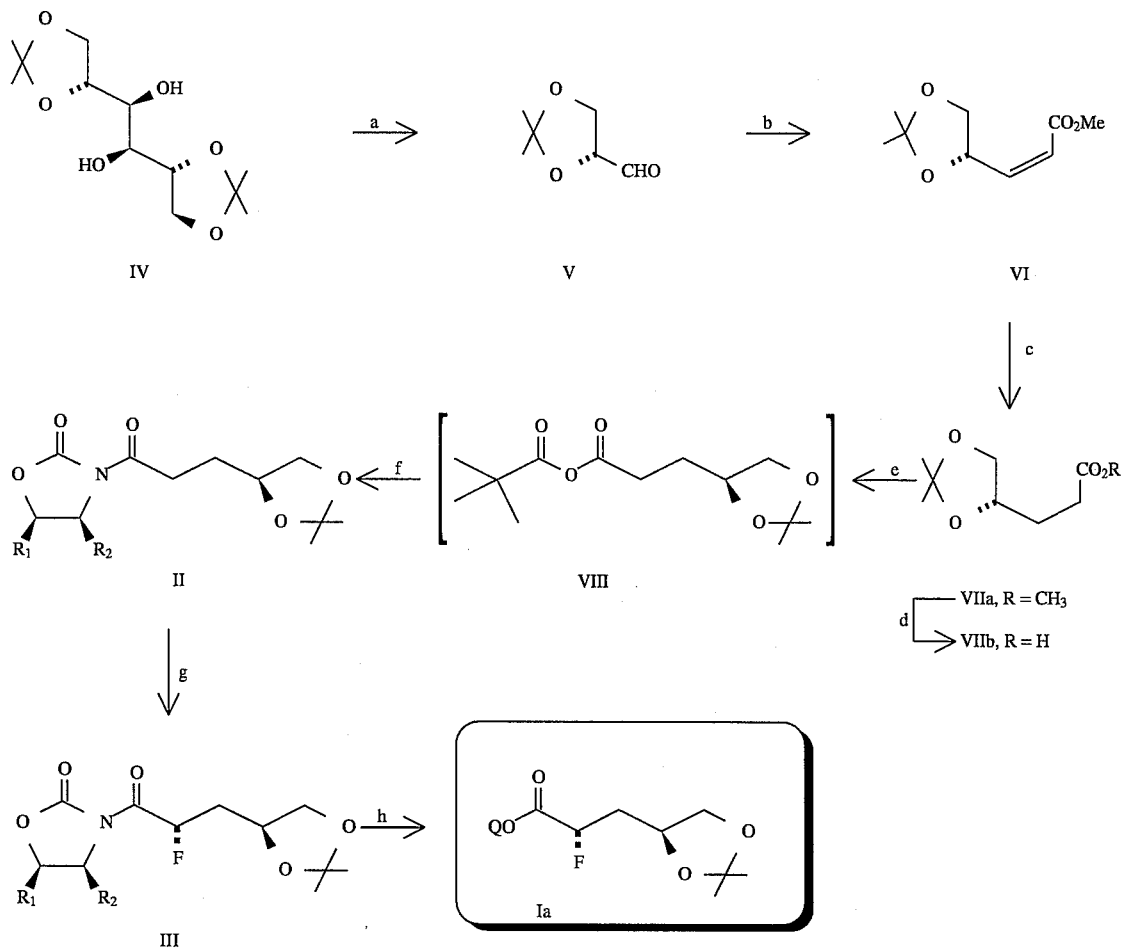

This synthetic route begins with the di-O-isopropylidene derivative of D-mannitol (IV). In step a of scheme A, 2,3-O-isopropylidine-D-(R)-glyceraldehyde (V) is generated by periodate cleavage. The periodate cleavage is carried out in the presence of periodate cleavage reagents and periodate cleavage reaction conditions which are generally known to those skilled in the art.

The glyceraldehyde V from the periodate cleavage reaction is reacted with the stabilized ylide, carbomethoxymethylene triphenyl-phosphorane, in step b to give methyl (S)-(Z)-4,5-O-isopropylidenepent-2-enoate of formula (VI) together with a small amount of trans/alkene. This step involves the use of the known Wittig reaction employing the known Wittig reagent and the usual Wittig reaction conditions.

The methyl ester (VIIa) was hydrolyzed in the presence of a base such as an alkali metal hydroxide or alkaline earth methyl hydroxide to give acid (VIIb), after neutralization with mineral acid such as, for example HCl or $H_2SO_4$.

A chiral oxazolidone of formula IX

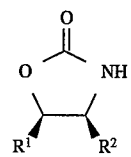

in which $R_1$ and $R_2$ are as defined, hereinabove was reacted as the metal (i.e., sodium, potassium or lithium) salt with the mixed anhydride (VIII) to give the chiral oxazolidone derivative of formula (II). The mixed anhydride was formed in situ by reaction of the acid (VIIb) with an appropriate acid anhydride or acid chloride. The anhydride was not isolated but reacted directly with the chiral auxiliary. While the pivaloyl mixed anhydride is shown in Scheme A, it is noted that other mixed anhydrides are also useful and encompassed within the scope of the present invention. In effect, the mixed anhydride can be prepared from an acyl halide or acyl anhydride in which the acyl moiety is a bulky group. Compound of formula (II) was fluorinated by conversion to the corresponding alkali metal enolate with a strong base such as, for example, alkali metal bis(trimethylsilyl) amide or lithium ethylamide and reaction with N-fluorobenzesulfonimide or N-fluoro-o-benzenedisulfonimide at low temperatures, such as, for example, below 0° C., more particularly at between about 0° C. to −80° C., most preferably at −78° C. to give the α-fluoro compound (III) with substantially complete diastereoselectively. The fluorination is normally carried out in our inert non-polar solvent, such as, for example, a dialkylether or cyclic ether such as tetrahydrofuran or dioxane.

The final step of present invention scheme A consisted of a mild alcoholysis of the compound of formula (III) to give the desired key intermediate ester of formula (Ia) and the reusable chiral oxazolidone auxiliary. The alcoholysis was carried out in the presence of Q magnesium bromide and the corresponding alcohol (QOH) in which Q is a group as defined above.

After the alcoholysis, a partial loss of the stereochemical integrity at C-2 was detected. It is believed that this occurred due to the acidity of the α-fluoro proton. The diastereoselectivity decreased slightly to 93% de as estimated by integration of the areas of the α-protons for both diastereoisomers in the $^1$H NMR spectrum.

The improved diastereoselectivity of the present method compares quite favorably with the 83.5% de reported by Okabe et al. in their synthesis. In spite of the slight loss in diastereoselectivity in the alcoholysis step, the instant method provides improved diastereoselectivity combined with an overall yield of about 25% from starting material (IV). This result clearly demonstrates the advantages of the instant method when compared to the 9.7% overall yield of (I) obtained from D-xylose by Okabe et al.

The compound of formula Ia can be converted to the fluorolactone X and to XI (2R, 3S, 5S)-2-chloro-3-fluoro-5 [triphenyl-methoxy)methyl] tetrahydrofuran.

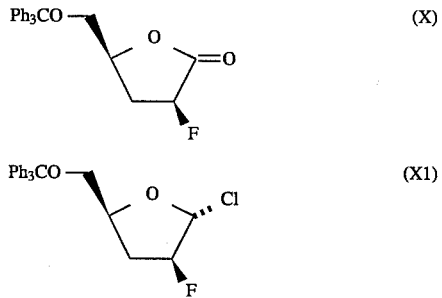

The compound of formula XI is an immediate precursor to both FddC and FddA. FddA can be obtained by the reaction of (XI) with the alkali metal salt of adenine.

The above reaction scheme A employs an oxazolidinone chiral auxiliary. However, other chiral auxiliaries which are capable of directing unidirectional fluoride addition such that an α-fluoro compound is provided with substantially complete diastereoselectivity may also be employed. One further such chiral auxiliary is the 1,3-thiazolidine-2-thione taught by Nagao et al. JACS, 1982, 104, 2079.

The following examples are illustrative for purposes of carrying out the instant invention and should not be construed as being limitations on the scope or spirit of the invention.

PREPARATION EXAMPLE 1

2,3-Isopropylidene-D-glyceraldehyde (V)

A suspension of commercially available 1,2:5,6-di-O-isopropylidene-D-mannitol (IV, 25 g, 0.0953 mol) in tetrahydrofuran:water (3:2, 85 mL) was treated with a solution of sodium periodate (22.3 g, 0.1043 mmol) in THF (240 mL). The mixture was stirred at room temperature for 3 hours until a white gelatinous precipitate formed. Ether (240 mL) was added and the mixture was filtered. The filtrate was concentrated under vacuum and dissolved in methylene chloride ($CH_2Cl_2$) (100 mL), dried with magnesium sulfate ($MgSO_4$), and finally concentrated under reduced pressure to give 22.8 g (92%) of crude product as an oil; 1H NMR ($CDCl_3$) δ 8.70 (d, J=1.5 Hz, 1H, CHO). This material was used in the following step without further purification.

PREPARATION EXAMPLE 2

Methyl (S)-(Z)-4,5-O-isopropylidenepent-2-enoate) (VI)

To a solution of the glyceraldehyde of preparation example 1 (2.03 g, 6.07 mmol) in methanol ($CH_3OH$) (10 mL) at 0° C. was added (in portions) methoxycarbonylmethylene(triphenyl)phosphorane (2.03 g. 6.07 mmol), and the mixture was allowed to reach room temperature while stirring over 1 hour. The solvent was removed and the residual oil was treated with hexane (50 mL) which induced precipitation of triphenylphosphine oxide. The mixture was filtered and the solid was washed with hexane (50 mL). The filtrate was cooled over ice to induce further precipitation of triphenylphosphine oxide and the mixture was again filtered. The final filtrate was concentrated to give 0.978 g (87.3%) of a colorless oil which according to NMR consisted principally of the major cis-product contaminated with traces of the trans-product. The 2H NMR spectrum of the product was identical to that reported in the literature (Mann, J.; Parlett, N. K.; Thomas, A. *J. Chem. Res.* 1987, 369) for the same compound.

PREPARATION EXAMPLE 3

Methyl (S)-4,5-O-isopropylidenepentanoate VIIa

To a solution of the ester of preparation example 2 (0.820 g, 4.4 mmol) in ethanol (25 mL) was added 10% Pd/C catalyst (0.050 g) and the mixture was hydrogenated in a Parr apparatus at 50 psi for 3 hours. The mixture was filtered through a celite pad and the filter cake was washed with methylene chloride. The filtrate was concentrated under reduced pressure and the crude product was purified by flash column chromatography (silica gel, 0→30% ethyl acetate in hexane) to give 0.713 g (86%) of the product as a colorless oil; 1H NMR ($CDCL_3$) δ 1.30 (s, 3H, $CH_3$), 1.38 (s, 3H, $CH_3$), 1.85 (m, 2H, H-3), 2.42 (m, 2H, H-2), 3.51 (dd, J=7.5, 6.6 Hz, 2H, H-$5_a$), 3.62 (s, 3H, $OCH_3$), 4.05 (m, 2H, H-$5_b$, H-4), $^{13}$C NMR δ 25.52, 26,82, 28.73, 30.11, 51.55, 68.97, 74.83, 108.94, 173.54.

PREPARATION EXAMPLE 4

(S)-4,5-O-isopropylidenepentanoic acid VIIb

A solution of the compound from preparation example 3 (21.98 g, 0.116 mol) in methanol (50 mL) was treated with a solution of lithium hydroxide monohydrate (7.9 g, 0.188 mol) in methanol:water (3:1, 200 mL) and the mixture was stirred at room temperature for 48 hours.

The methanol was removed under reduced pressure and water and 5% aqueous HCl was added to adjust the pH to ca. 6. Following multiple extractions with chloroform (3×75 mL) the organic layer was dried with anhydrous sodium sulfate ($Na_2SO_4$) and concentrated under reduced pressure to give 14.54 g (72%) of an oily product. An additional amount of product (5.01 g, 25%) was obtained after re-neutralization of the aqueous layer and further extraction with chloroform; 1H NMR ($CDCL_3$) δ 1 30 (s, 3H, $CH_3$), 1.40 (s, 3H, H-$5_a$), 1.85 (m, 2H, H-3), 2.50 (m, 2 H, H-2), 3.55 (dd, J=7.7, 6.6 Hz, 1H, H-$5_b$), 4.10 (m, 2H, H-$5_b$, H-4); $^{13}C$ NMR δ 25.51, 26.82, 28.44, 30.13, 68.94, 74.72, 109.20, 179.13.

PREPARATION EXAMPLE 5

(4S,5R)-3-[(S)-1-oxo-4,5-O-isopropylidenepentyl]-4-methyl-5-phenyl-2-oxazolidinone (II)

A solution of the acid from preparation example 4 (7.15 g, 41.05 mmol) and trithylamine (7 mL, 5.08 g, 50.22 mmol) in dry tetrahydrofuran (200 mL) at −78° C. was treated with pivaloyl chloride (6.2 mL, 6.07 g, 50.50 mmol). The resulting mixture (containing precipitated triethylamine hydrochloride and the corresponding mixed anhydride) was stirred at that temperature for an additional 30 minutes. Separately, a solution of commercially available (4S,5R)-4-methyl-5-phenyl-2-oxazolidinone (7.43 g, 42.4 mmol) in tetrahydrofuran (100 mL) at −78° C. was treated with a solution of n-BuLi in tetrahydrofuran (1.6M. 25.5 mL. 40.8 mmol) with additional stirring at −78° C. for 1 h. This solution was then added carefully to the cold (−78° C.) anhydride-containing suspension and the entire mixture was stirred just at −78° C. for 1 h and then at room temperature for 2 hours more before quenching with a solution of ammonium chloride (100 mL). The volatiles were removed and the residue was extracted with chloroform (3×100 mL). The combined organic extract was washed with 5% aqueous sodium bicarbonate (3×75 ml) and dried ($Mg_2SO_4$). The solvent was removed and the crude product was purified by flash column chromatography (silica gel, 0→30% ethyl acetate in hexane) to give 11.58 g (81%) of product as a thick oil; 1H NMR ($CDCl_3$) δ 0.90 (d, J=6.6 Hz, 3H, oxazolidinone 4-Me), 1.32 (s, 3H, $CH_3$), 1.40 (s, 3H, $CH_3$), 1.95 (m, 2H, H-β), 3.10 (m, 2H, H-α), 3.60 (dd, J=7.8, 6.8 Hz, 1 $H_3$, H-$5_a$), 4.05 (dd, J=7.8, 6.1 Hz, 1H, H-$5_b$), 4.15 (m, 1H, H-4), 4.75 (m, 1H, oxazolidinone H-4), 5.65 (d, J=7.3 Hz, 1H, oxazolidinone H-5), 7.20–7.50 (m, 5H, oxazolidinone 5-Ph); $^{13}C$ NMR δ 14.53, 25.64, 26.94, 28.21, 32.07, 54.77, 69.18, 74.96, 79.03, 109.02, 125.62, 128.71, 128.77, 133.25, 153.00, 172.43.

PREPARATION EXAMPLE 6

(4S,5R)-3-[(2S,4S)-1-oxo-2-fluoro-4,5-O-isopropylidenepentyl]-4-methyl-5-phenyl-2-oxazolidinone (III)

A solution of the oxazolidinone derivative of preparation example 5 (1.03 g, 3.09 mmol) in tetrahydrofuran (15 mL) at −78° C. was stirred under a nitrogen atmosphere and treated with a cold solution (ca. 4° C.) of sodium bis(trimethylsiLyl)amide in tetrahydrofuran (1.0M, 3.5 mL, 3.5 mmol). After 30 minutes, a cold solution (ca. 4° C.) of commercially available N-fluorobenzenesulfonimide (0.94 g, 2.98 mmol) in tetrahydrofuran (5 mL) was added and the resulting mixture was stirred at −78° C. for 2 hours. While still at that temperature, the reaction was quenched with a saturated solution of ammonium chloride (5 mL) which induced the precipitation of a solid. After the reaction was allowed to reach room temperature and the precipitate disappeared, the volatiles were removed under reduced pressure. The residual material was partitioned between methylene chloride (50 mL) and water (25 mL) and the aqueous layer was extracted twice with methylene chloride (2×25 mL). The combined organic extract was washed with water (50 mL), dried ($Na_2SO_4$), and reduced to dryness to give a crude product that was purified by flash column chromatography (silica gel, 0→30%, ethyl acetate in hexane) to give 0.679 g (62%) of the desired product as a thick oil; $^1H$ NMR ($CDCl_3$) δ 0.95 (d, J=6.6 Hz, 3H, oxazolidinone 4-Me), 1.32 (s, 3H, $CH_3$), 1.45 (s, 3 H, $CH_3$), 1.90–2.40 (m, 2H, H-β), 3.65 (ddd, J=8.3, 5.8, 0.7 Hz, 1H, H-$5_b$), 4.40 (m, 1H, H-4), 4.75 (m, 1H, oxazolidinone H-4), 5.70 (d, J= 7.3 Hz, 1H oxazolidinone H-5), 6.15 (ddd, J=49.4, 9.2, 3.6 Hz, 1H, H-α) 7.20–7.50 (m, 5H oxazolidinone 5-Ph). This NMR shows that the product is contaminated with ca. 10% of compound II. Further chromatographic purification of this material gave an analytical sample. Anal. Calc $C_{18}H_{22}FNO_5$: C, 61.53; H, 6:31; N, 3.98, Found: C, 61.65; H, 6.38; N, 3.99.

PREPARATION EXAMPLE 7

(S-S-α-fluoro-2,2-dimethyl-1,3-dioxolane-4-propanoic acid methyl ester (I)

A solution of methylmagnesium bromide (3.0M, 0.2 mL, 0.6 mmol) was added dropwise into dry methanol (2 mL) at 0° C. After stirring the suspension for 15 min under nitrogen, a solution of the compound of preparation example 6 (0.10 g, 0.284 mmol) in anhydrous methanol (3 mL) was added. The suspended material went into solution and the reaction mixture was stirred further for 1 hour at 0° C. The addition of 3 mL of pH 7 phosphate buffer quenched the reaction which was later partitioned between saturated brine (20 mL) and $CH_2Cl_2$ (30 mL). The aqueous layer was further washed with $CH_2Cl_2$ (30 mL). The aqueous layer was further washed with $CH_2Cl_2$ (2×25 mL) and the combined organic extract was dried ($Na_2SO_4$), concentrated, and purified by flash column chromatography (silica gel, 0→20%, ethyl acetate in hexane) to give 0.49 g (83.6%) of the desired product as an oil: $^1H$ NMR ($CDCl_3$) δ 1.37 (s, 3H, $CH_3$), 1.43 (s, 3 H, $CH_3$), 2.00–2.30 (m, 2H, H-β), 3.60 (dd, J=8.0, 6.5 Hz, 1H, H-$5_a$), 3.82 (s, 3H, $OCH_3$), 4.10 (dd, J=8.0, 6.2 Hz, 1 $H_1$ H-$5_b$), 4.30 (m, 1H, H-4), 5.12 (ddd, J=49.3, 10.2, 2.5 Hz, 1H, H-α). This $^1H$ NMR spectrum was identical to that reported by Okabe et al. When the sample was dissolved in $C_6D_6$ and the δ 4.50–5.50 region was expanded, the ddd signal form H-1 in the trans-isomer the dt signal from the same proton in the syn-isomer were completely separated. The anti:syn ratio based on the NMR integration was 26:1, which corresponds to a de of 93%. This value is better than the de 83.5% obtained by Okabe et al.

We claim:

1. A compound of the formula

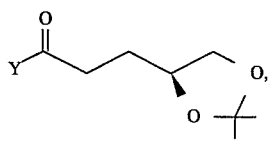

in which Y is an oxazolidinone group of the formula:

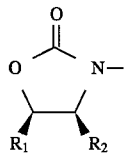

in which $R_1$ is H methyl, ethyl, propyl, isopropyl, butyl, sec. butyl, tert. butyl, phenyl, or benzyl and $R_2$ is methyl, ethyl, propyl, isopropyl, butyl, sec. butyl, tert. butyl, phenyl or benzyl.

2. The compound according to claim 1, in which $R_1$ is methyl and $R_2$ is phenyl or in which $R_1$ is phenyl and $R_2$ is methyl.

3. A compound of the formula

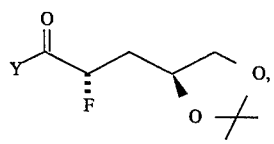

in which Y is an oxazolidinone group of the formula:

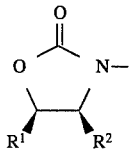

in which $R_1$ is H methyl, ethyl, propyl, isopropyl, butyl, sec. butyl, tert. butyl, phenyl, or benzyl and $R_2$ is methyl, ethyl, propyl, isopropyl, butyl, sec. butyl, tert. butyl, phenyl or benzyl.

4. The compound according to claim 3, in which $R_1$ is methyl and $R_2$ is phenyl or in which $R_1$ is phenyl and $R_2$ is methyl.

* * * * *

UNITED STATES PATENT AND TRADEMARK OFFICE
CERTIFICATE OF CORRECTION

PATENT NO. : 5,498,719
DATED : March 12, 1996
INVENTOR(S) : Victor Marquez, et. al.

It is certified that error appears in the above-indentified patent and that said Letters Patent is hereby corrected as shown below:

Title page, item [75], inventor: Delete "Magbool A. Siddiqui" and insert -- MAQBOOL A. SIDDIQUI __.

Signed and Sealed this

Nineteenth Day of November, 1996

*Attest:*

BRUCE LEHMAN

*Attesting Officer*     *Commissioner of Patents and Trademarks*